United States Patent [19]

Miwa

[11] Patent Number: 4,483,345
[45] Date of Patent: Nov. 20, 1984

[54] PRESSURE MEASURING SYSTEM WITH ULTRASONIC WAVE

[75] Inventor: Hirohide Miwa, Kawasaki, Japan

[73] Assignee: Fujitsu Limited, Kawasaki, Japan

[21] Appl. No.: 405,143

[22] Filed: Aug. 4, 1982

[30] Foreign Application Priority Data

Aug. 8, 1981 [JP] Japan ............................. 56-124588

[51] Int. Cl.$^3$ ............................................. G01N 29/02
[52] U.S. Cl. ........................................ 128/662; 73/19
[58] Field of Search .......................... 73/19, 702, 703; 128/662

[56] References Cited

U.S. PATENT DOCUMENTS

| | | | |
|---|---|---|---|
| 3,622,958 | 11/1971 | Tucker | 73/19 |
| 3,640,271 | 2/1972 | Horton | 138/662 |
| 3,974,681 | 8/1976 | Namery | 73/19 |
| 4,112,735 | 9/1978 | McKnight | 73/19 |
| 4,122,713 | 10/1978 | Stasz et al. | 73/19 |
| 4,130,010 | 12/1978 | Wonn | 73/19 |

FOREIGN PATENT DOCUMENTS

| | | | |
|---|---|---|---|
| 2946662 | 5/1981 | Fed. Rep. of Germany | 128/662 |
| 725014 | 3/1980 | U.S.S.R. | 73/19 |

OTHER PUBLICATIONS

Rasor Associates Inc., Noninvasive Assessment of Pulmonary Hypertension Using the Bubble Ultrasonic Resonance Pressure Method, Apr. 1977.
Devine, III et al., Noninvasive Pressure Measurement, IBM Corp., 1978.
Jacobson, Ultrasonic Detection of Blood Stream Emboli, Sep. 1973.
Nashi, Ultrasonic Detection of Bubbles With Doppler Flow Transducers, Jul. 1972.

Primary Examiner—Stephen A. Kreitman
Assistant Examiner—Hezron Williams
Attorney, Agent, or Firm—Staas & Halsey

[57] ABSTRACT

A system for measuring from the outside of a living body the pressure within the heart or the pressure of any portion which does not allow a measurement by the direct insertion of a pressure measuring sensor.

This system provides a method of measuring the pressure of the object by generating fine bubbles through cavitation, applying a low frequency ultrasonic wave to the medium, and then detecting the bubbles which are generated with a system for detecting the high or low frequency harmonics due to the bubbles or a higher frequency ultrasonic wave applied to the medium.

38 Claims, 8 Drawing Figures

FIG. 1.
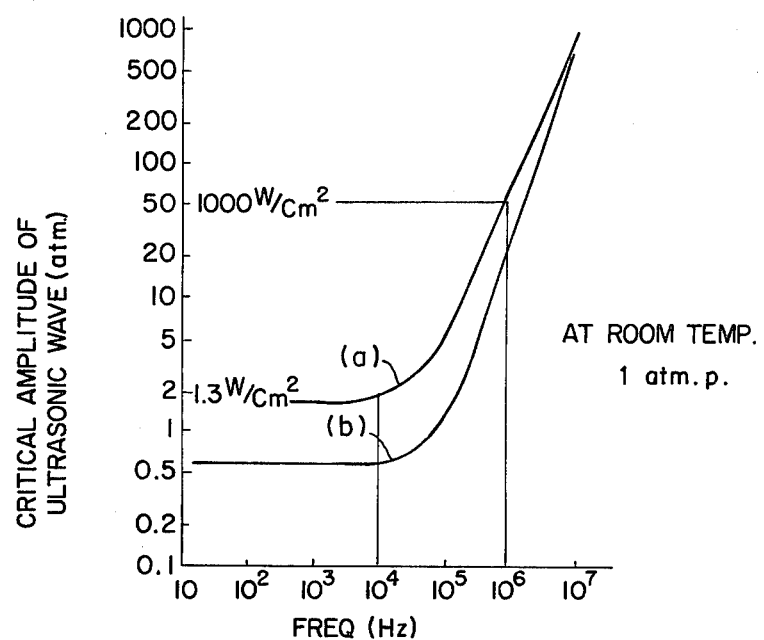
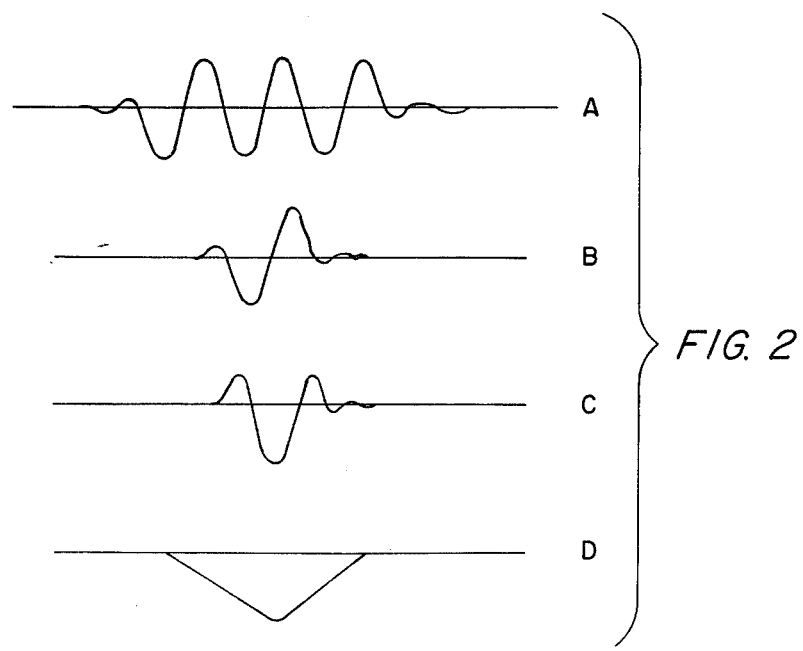
FIG. 2

PRESSURE MEASURING SYSTEM WITH ULTRASONIC WAVE

BACKGROUND OF THE INVENTION

The present invention relates to a liquid pressure measuring system. Particularly, to a system for non-destructively measuring fluid pressure from outside the body containing the fluid, by the use of ultrasonic waves. For example, blood pressure in the heart of a living body or the pressure of flowing liquid used in the chemical industry to show particularly high temperature and pressure, the high probability of a chemical reaction or the existence of solid particles or fibres etc., in cases where it is difficult to insert a pressure gauge directly into a measuring object.

Currently, a catheter equipped with a pressure sensor has been inserted into the blood vessels or heart in order to measure blood pressure. This method is accompanied by the disadvantages of creating pain and a risk to life by the unexpected misoperation or by infection. The methods of acoustically detecting a blockage of the blood flow in the arm or detecting the start of a pulse by winding a cuff around the arm and changing the air pressure are also known. This method using a cuff can be applied to the arms and legs but cannot be used for measurement of internal organs such as the heart.

In the field of industrial systems operating at a high temperature, a low temperature, and/or in a strong radiation field, and the handling of liquids which are chemically active, of high viscosity, or of a dense mixture of grain particles, chips of wood and fibres etc. pressure sensors have often been damaged by temperature, radiation, chemical reaction or by external force due to solid materials. Therefore, it is desired to measure pressure from outside of a vessel or system but there has been no adequate method.

SUMMARY OF THE INVENTION

An object of the present invention is to provide a method of non-destructively measuring the pressure of a desired region within a substance, from outside, by the following process. Ultrasonic waves are applied to the desired region within a substance, to generate bubbles within the liquid existing in the region during the negative pressure cycle of the ultrasonic waves and, thereafter, the generation of bubbles is detected by harmonic or subharmonic ultrasonic waves which accompany such bubbles and/or by the echo of other ultrasonic waves of higher frequency applied to the region.

Generally, ultrasonic waves are sound waves of a frequency higher than the audible frequency (16 kHz) but the present invention is meant to include audible sound waves and ultrasonic waves in the sense mentioned above.

The present invention utilizes cavitation, a method by which the gas and/or water content of the blood, lymph and cell liquids etc. existing in the heart, blood vessels or organs of a human body are isolated or vaporized by the negative pressure of the externally applied ultrasonic waves to generate micro bubble nuclei which then grow in to larger bubbles.

BRIEF DESCRIPTION OF THE DRAWINGS

FIG. 1 is a graph indicating the relation between the critical sound pressure and frequency for generating the cavitation.

FIG. 2 illustrates waveforms typical of the sound pressure to be applied.

DESCRIPTION OF THE PREFERRED EMBODIMENT

Figure 3:
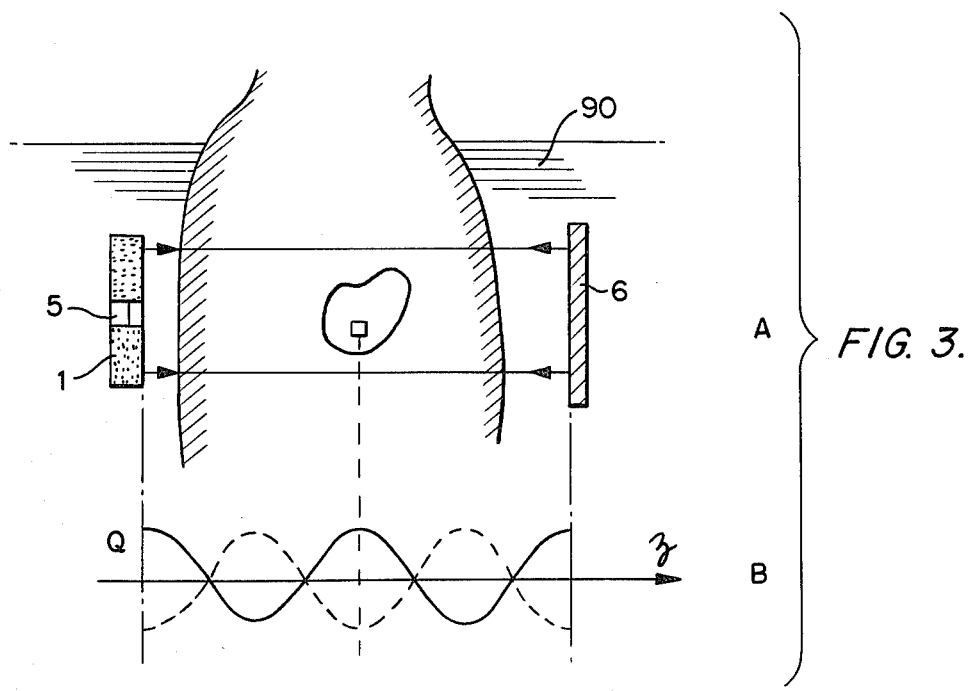
FIG. 3A is a sectional view and FIG. 3B is a pressure distribution diagram indicating an embodiment which forms a pressure sweep at the measuring area in a human body etc. with standing waves.

The critical pressure of bubble formation is a function of the ambient pressure (about 1 atm at sea level), the temperature, the frequency of ultrasonic waves applied and the type of waves, for example progressive or standing waves. It is also required that the liquid to be measured has been sufficiently degassed or on the contrary has been exposed to or absorbed the gas sufficiently.

As an example, FIG. 1 shows the measurement of the critical amplitude of ultrasonic waves used for generating bubbles under an ambient pressure of 1 atm at room temperature. FIG. 1(a) relates to sufficiently degassed water and FIG. 1(b) relates to sufficiently airated water. The horizontal axis indicates the frequency, while the longitudinal axis indicates the sound pressure (amplitude). The profile changes in the frequency zone of about $10^4$ to $10^5$ Hz. At frequencies under $10^4$ Hz, the critical pressure for generating bubbles does not depend on the frequency, but it is highly dependent on the frequency at $10^5$ Hz or higher. This indicates that a time of about $10^{-4}$ seconds is necessary for formation of nuclei and growth of bubbles.

In past methodologies, it has been impossible to accurately measure the critical pressure for formation of bubble nuclei. It has been measured by optically recognizing the bubbles or by the accoustic sound generated when the bubbles grow and break. These methods result in a time lag during growth of the bubbles between the application of pressure and the detection of bubbles, and therefore, fluctuation of critical pressure measurement is induced and some delay in the response time is caused. In the case of the present invention, bubbles are detected in the early stage of growth as bubble nuclei thereby resulting in an improvement of measuring accuracy and a decrease in the response time.

The bubble nuclei differ from the liquid in accoustic impedance and give an intensive reflection and scattering of ultrasonic waves. The bubble nuclei are generally equal to or smaller than the wavelength of the applied waves, in the frequency range from 1M to 10 MHz, and generate a Rayleigh scattering. The wave energy of ultrasonic waves is proportional to the square of frequency. Therefore, the higher the frequency is, the higher the sensitivity is. But, the ultrasonic waves are exponentially attenuated as they are transmitted into a living body and the attenuation coefficient of a living body is almost proportional to the frequency. If the frequency is high, the ultrasonic waves suffer the same attenuation during forward and backward transmission for the detection of nuclei bubbles at the deeper region of the human body. Therefore, ultrasonic waves of 1 MHz to 10 MHz are suitable for detection of bubbles within a human body.

Reflected waves can be easily distinguished, in the case of measuring blood pressure, within the heart or within large blood vessels because the waves reflected from the blood are weak but intensively reflected waves appear due to the bubble generation. It is, however difficult to distinguish the bubble generation because intensive waves reflected from the structural tissues coexist with the bubbles such as the regions near blood vessel walls, small blood vessels, lymph vessel and tissue fluid. Even in such a case, if the liquid is flowing, the reflected waves have a Doppler shift due to the flow of the bubble nuclei. An embodiment of the present invention provides a system of eliminating the effect of reflections from the structual organs by extracting such Doppler shifts a method of detecting bubble generation with a Doppler signal and also, as a result, a highly sensitive measurement. This system simultaneously measures both flow rate and pressure, resulting in the attainment of highly accurate and detailed data.

As explained above, measurement of the critical pressure for bubble formation according to the present invention becomes more accurate and the time delay, when an applied pressure is swept, is almost eliminated. Therefore the sweep speed can be increased while still detecting the generation of bubble nuclei with a high sensitivity.

A method of sweeping the applied pressure can be selected freely, but it is easy to utilize a pressure amplitude which changes in relation to a sine wave. For this method, a continuous wave or a burst of waves illustrates in FIGS. 2A, B, and FIG. 2 or a pulse wave, illustrated in FIG. 2C, can be used. In this case, wider band widths are necessary in the sequence of A, B and C around the center frequency f. Moreover, it is also possible to perform the sweep using a saw-tooth wave as illustrated in FIG. 2D.

It is desirable to set the center frequency f, from FIG. 1, at 10 kHz or less because the bubble nuclei generating pressure can thereby be lowered. The high sensitivity nuclei bubble detection of the present invention allows the use of higher frequency ultrasonic waves for nuclei bubble generation but it is desirable to be able to ignore the attenuation within a human body and consequently it is desirable to select a frequency of 1000 kHz or less. Attenuation by tissue is of the order of 1 db/MHz.cm and, therefore, an attenuation of 0.2 db is expected when ultrasonic wave of 10 kHz are irradiating an area located 20 cm from the surface of a human body and such attenuation can almost be ignored.

In the following explanation, blood is used as the measuring liquid. The blood pressure in the heart rapidly changes and this change is denoted as $P_p(t)$ for each pulsation Reference is made to the ambient pressure $P_a$ (generally atmospheric pressure) and the current object is to measure $P_p(t)$ non-invasively, i.e., from the outside of body. Generation of nuclei bubbles in blood by the cavitation can be thought of as depending on the absolute pressure when the rate of gasification, such as dissolution and absorption of gas is constant and the temperature is constant. Such a critical pressure is denoted as $P_c$. The absolute pressure of blood is denoted as $P(t)$, which is always changing due to pulsation. The following relation can thus be obtained.

$$P(t) = P_p(t) + P_a$$

Where, $P_a$ is changing very little over several hours and $P_p(t)$ indicates the change by pulsation which is slower, on the order of msec, for each pulse. Here it is supposed that a sound field denoted as $Q(t)$ is applied to the measuring area, which is given by the next equation.

$$Q(t) = -Q_0 \cdot \sin(2\pi f t) \quad (0 \leq \pi f t \leq \pi)$$

Where, the frequency f is selected, for example, about 10 kHz so that $Q(t)$ changes at a faster rate than $P_p(t)$.

The combined absolute pressure $\tilde{P}(t)$ is denoted as follows.

$$\tilde{P}(t) = P(t) + Q(t)$$
$$= P_p(t) + P_a - Q_0 \cdot \sin(2\pi f t)$$

When $Q_0$ is selected properly in order to cause $\tilde{P}(t)$ to decrease to $P_c$ (critical pressure) or less in the negative cycle of $Q(t)$, nuclei bubbles are generated in the range where $\tilde{P}(t) \leq P_c$ and at the time $t_c$, when $\tilde{P}(t) = P_c$, the following relations can be obtained.

$$P_c = P_p(t_c) + P_a - Q_0 \cdot \sin(2\pi f t_c)$$
$$\therefore P_p(t_c) = Q_0 \cdot \sin(2\pi f t_c) - (P_a - P_c)$$

Accordingly, $P_p(t_c)$ can be obtained when the values of $Q_0$, $t_c$, $P_a$, $P_c$ are known. Here, $Q_0$, $t_c$, $P_a$ can be measured and $P_c$ can be obtained by calibrating the result of a measuring method as explained later.

The critical pressure $P_c$ can be obtained previously in the case of industrial systems, but it may change when chemical reactions continue during a step by step process or as in the human body, the temperature or degree of gasification may change over time due to changing conditions, for example, exercise, sleeping, etc. or between individuals. Explained below is a method for determining $P_c$ of the blood of a human body, as an example.

In the case of blood flow within a human body, which circulates in the closed loop, blood having the same temperature and rate of gasification as the main measuring area can be found in other areas. For example, the blood in the left ventricle of the heart can be though of as flowing into the arteries of the upper arm and the blood in the veins of the upper arm can be assumed to have the same temperature and rate of gasification as that of the right ventricle. However, the blood exchanges substances at the vasal capilaries of the lungs and tissues and therefore its characteristics change as it passes through them. For this reason, when the critical pressures of the arteries and viens of the upper arms can be obtained, the pressures in the left atrium and the left ventricle of the heart (artery blood) and the right atrium and the right ventricle (vein blood) can be measured. The artery pressure $P_p'$ of the upper arm is often measured by the following procedures. A rubber air tube is wound aroud the arm to temporarily block the flow of blood by increasing the air pressure in the tube. The pulsating condition is then monitored with an acoustic receiver while the air pressure is gradually decreased and the maximum blood pressure $P_p'$ max is measured by accoustically detecting the sound generated when the peak pulse flow returns. The minimum blood pressure, $P_p'$ min, is found by detecting the sound generated when the lower limit of the pulse flows returns. Generally, the maximum blood pressure can be measured with higher accuracy and it is desirable to calibrate the critical pressure with this value.

The vein pressure and tissue liquid pressure can be measured directly by inserting a pressure sensor into the blood vessel or tissue; this is much safer than insertion into an artery.

First, the $P_p'$ max is measured at the upper arm portion and thereafter the same arm portion is measured under the same condition by the method of the present invention. Thus, a value of $P_c$ can be obtained by assuming that the result of the measurement is equal to $P_p'$. In the case of industrial systems, the value of $P_p$ for the measuring can be determined by calibrating $P_c$ at a more feasible and safer region.

Moreover, the necessary applied pressure $Q_0$ can be lowered, thereby improving the response time by previously dissolving or absorbing harmless gas which easily forms bubbles, such as a noble gas like helium or carbon dioxide into the blood. These gases can be dissolved into the blood during breathing by placing the body in an atmosphere where part of the nitrogen is replaced by helium or carbon dioxide or by increasing the pressure of the ambient mixture. It is also possible to introduce gas directly into the blood vessels by injecting well gasified or volatile liquid. As explained above, measurements can be made with a small $Q_0$ if the critical pressure $P_c$ is increased. Moreover, the response time is improved and the number of repetitions of the measuring sweep can be increased. Reduction of $Q_0$ not only makes easy and economical the designing of unit, but also minimizes the effects of the ultrasonic waves on a human body.

The desired timing and area of measurement can be obtained, and noise and unwanted signals can be eliminated, by synchronizing the application time and the area and measuring time and area so that the ultrasonic waves for detecting bubbles are applied to the measuring area only when the negative sweep of pressure is interacting with the measuring area.

An embodiment applied to a human body is explained hereunder.

Figure 4:
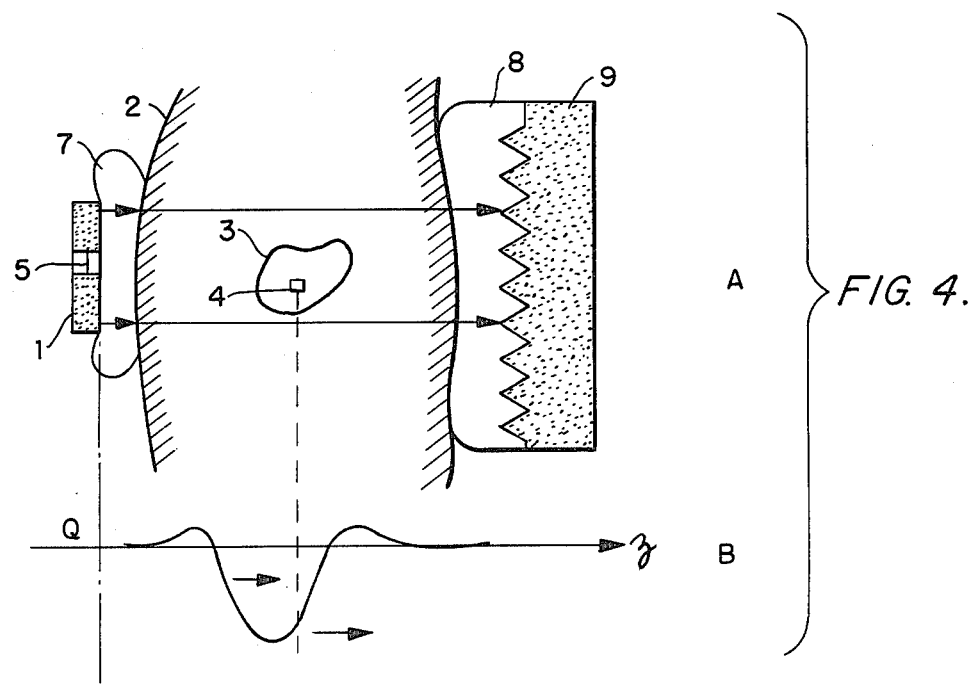
FIG. 4A is a sectional view and FIG. 4B is the corresponding pressure distribution diagram indicating an embodiment using a progressing wave.
Figure 5:
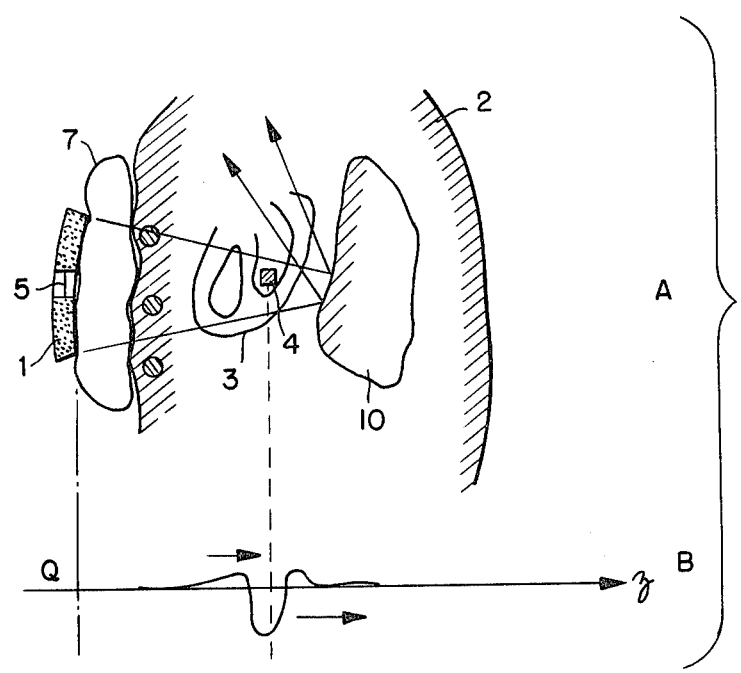
FIG. 5A is a sectional view and FIG. 5B is a pressure distribution diagram indicating an embodiment using a progressing wave.

FIG. 3 and FIG. 4 show the methods of forming the ultrasonic wave amplitude which is applied to areas which do not prevent transmission of the ultrasonic waves, such as the abdomen and arms or legs. FIG. 5 shows the method which can be applied to the case where the ultrasonic waves cannot pass through the body because a lung, containing air, exists behind the heart. The lung becomes an intensive reflector due to the large difference in the accoustic impedance between the air and tissue, and therefore, the ultrasonic waves can not pass through the body.

The transducer 1 forming the sweep pressure is driven, for example, at a center frequency of 10 kHz. If the ultrasonic waves are applied to a human body, a transducer diameter of 50 to 200 mm is most desirable. A hole of about 15 to 25 mm in diameter is provided at the center in order to mount the bubble detection send/receive transducer 5. A human body 2 and a particular tissue 3 such as the heart, liver or artery surround the measuring area 4. The dimension of the measuring area 4 is determined by the beam diameter of the bubble detection ultrasonic waves and the drive pulse length or the gate width for extracting the measuring signal from the reflected signal with the timing gate. The the bubble detection send/receive transducer 5 has a center frequency of, for example, 3.5 MHz. The diameter required for obtaining a sufficiently converged beam is about 10 mm. For humans, the size of the measuring area 4 can be set to several millimeters.

FIG. 3A shows the example where 1, 5, and 2 are respectively arranged within water 90 which is a sound conductive medium. A reflector 6 consisting of a metal plate, having an acoustic impedance which is greatly different from that of water or a living body is arranged within the water opposite to the transducer 1 with the distance of n×half-wavelength ($\lambda/2$). Simultaneously the transducer 1 transmits a continuous wave of wavelength $\lambda$. Thereby creating a resonant condition between the transducer 1 and the metal plate 6, thus forming a standing wave as shown in FIG. 3B.

When the frequency is 10 kHz, the wavelength in the water or a living body is 15 cm. If, for example, n is 4 the distance between the transducer 1 and the metal plate 6 becomes 30 cm (15/2×4). This is sufficient for placing the abdomen of a human body between the transducer 1 and the plate 6. The vibration loop center of the standing wave can be set to the measureing area by shifting the transducer 1 and the plate 6 in relation to the abdomen 2 while keeping the distance between the transducer 1 and the plate 6 at a constant value. As the pressure in the area changes with the sine wave of 10 kHz, the maximum pressure amplitude of which is the amplitude of loop, generation of nuclei bubbles can be obtained by using a half cycle of negative swing for the pressure sweep.

FIG. 4 is an example of the use of a progressing wave. A plastic bag 7 containing water is used in place of the water in FIG. 3. This plastic bag exists between the transducer 1 and the body 2 such as the abdomen of a human body. Jelly or oil is applied at the contact surface in order to obtain transmission of the ultrasonic wave by eliminating the air. Another plastic bag 8 containing water, and a non-reflective absorber of ultrasonic waves 9 consisting of a plastic or rubber containing metallic powder or bubble corpuscles is placed on the other side of the body. is placed on the other side of the body 8 and the absorbant material 9 are integrated and the jelly or oil is applied at the contact surface between the body 2 and the water bag 8 in order to eliminate any air gaps. When the transducer 1 transmits the pulse wave as shown in FIG. 2C, the pulse wave progresses into the absorbant material 9 from the transducer 1 at the velocity of sound in water (about 1500 cm/sec) and is absorbed. FIG. 4B shows the of pressure value at a particular moment during its transmission. When looking at the particular measuring area, for example, the area 4, the pressure varies with the same waveform as the waveform transmitted by the transducer 1, but it is delayed by a time obtained by dividing the distance between the transducer 1 and the measuring area 4 by the velocity of sound and changes with time. Namely, a pressure sweep is carried out.

Figure 7:
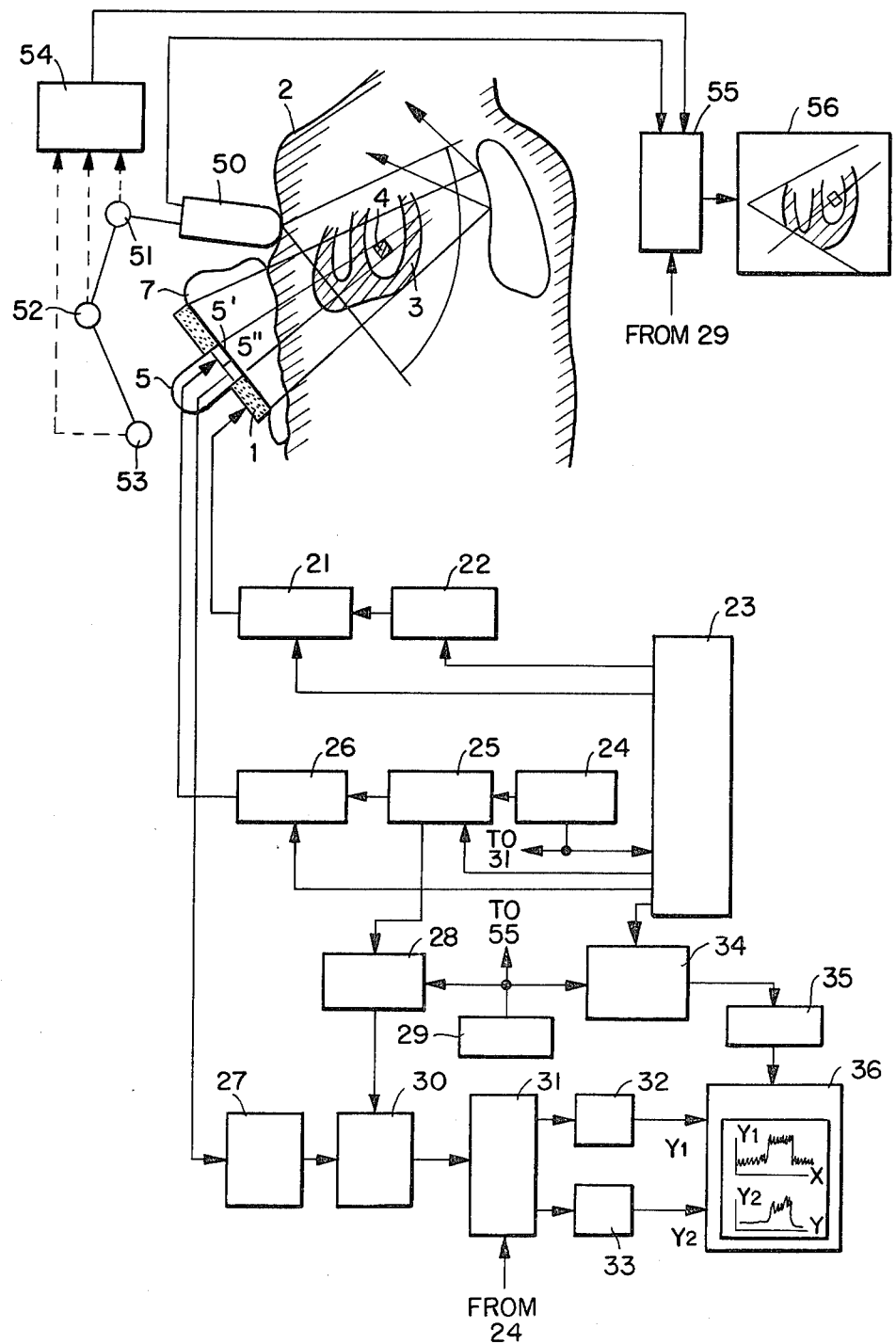
FIG. 7 is a block diagram of a system of an embodiment using a continuous wave modulated by an M sequence code, as the bubble detecting ultrasonic wave, to measure a changing blood pressure in real time while confirming the measuring region on B mode image of the human heart.

FIG. 5 shows the case where a strong absorber or reflector, like a lung, exists behind the measuring area 4, such as the heart. In the case where a strong absorber exists behind the measuring area, the situation is similar to the case of FIG. 4. But if there is an strong reflecting surface 10 behind the measuring area, the sweep pressure at the measuring area 4 becomes uncertain because the pressure field is formed at the area 4 by both the reflected waves from the reflecting surface 10 and the field of progressing wave from the transducer 1. In order to prevent such overlapping, the width of the progressive wave must be shortened by setting its center frequency at 100~1000 kHz and the wave propagation direction (incident direction) must also be changed as shown in FIG. 7. The existence and location of a reflecting body can be detected by using the transducer 1 as the receiver or by the transducer 5. FIG. 5B shows the pressure distribution at a particular moment.

In any case, the size of the transducer 1 (diameter) cannot be too large for practical use and therefore the diameter becomes almost equal to the wavelength and, as a result, the wave generated becomes similar to a spherical wave.

In FIG. 3, the transducer 1 must supply a drive energy large enough to compensate for the energy spherically diverging in directions other than towards the plate 6 in order to obtain a resonance between the transducer 1 and the plate 6. In FIG. 4, and FIG. 5, the transmitter surface of 1 is not required to be flat and can be formed as a concave surface in order to converge the energy in the required direction. In any case, the pressure amplitude along the axis perpendicular to the face of the transducer 1 changes as a function of distance z and therefore it is necessary to determine the function, by setting the transducer 1 in water without a human body 2 and measuring the pressure as the function of the axial distance z.

The bubble detection transducer 5 can be flat or concave and can also be a phased array type of multielements. As the material, structure, circuit etc., those used by the so-called A mode, M mode, B mode and Doppler measurement can be used.

As shown in FIG. 7, the measuring area can be determined while observing the sectional view of the B mode. For this purpose, the method similar to the well known Doppler measurement combining the B mode can be used.

In this case, since the applied pressure sweep frequency is sufficiently low, simultaneous operation with the bubble detecting system can be realized without any interference between them. On the contrary, the B mode and bubble detection frequencies are sufficiently high, so any influence or interference on the low frequency critical pressure does not occur. This can be understood from FIG. 1.

The transducer 5 can be mounted in a port of transducer 1 as indicated in the figure, or it can be mounted in a location other than the port of that transducer 1. If the B mode is used in combination the sector scanning can be done by 5 itself and the scanning for detecting bubbles passing the measuring area 4 may be done during the scanning. Moreover, it is also possible to use another B mode probe as shown in FIG. 7.

If the measuring area 4 is located in the tissue cell, the Doppler effect cannot be used because the measuring area 4 will have no blood flow and detection must be made by extracting the change of the reflection intensity. For example, when a burst of waves (having a duration of about 1 μs) with a center frequency of 3.5 MHz is transmitted from the transducer 5, the pulse becomes a burst wave of about 1.5 mm in length and progresses at a rate of about 1.5 mm/μs. As the pulse progresses, reflected waves are sent back from each point in accordance with changes in the accoustic impedance. Therefore, the received waveform at transducer 5 is continuous and complicated. But, observations can be made by only receiving the waveform reflected from the position of the measuring area 4 by extracting that signal with a timing gate. This is ordinarily well known. The one reflected signal from the measuring area 4 can be obtained for a single scanning as explained above. Namely, when the measuring area 4 is located at the depth of about 20 cm within a body, the time required for the forward and backward transmission of ultrasonic wave is 266 μs and measurements can be made 3760 times per second. As explained above, when the measuring area 4 is located in the flow of the heart or a blood vessel not only the simple reflection intensity but also the Doppler shift caused by blood flow can be analyzed and detected by a well known method such as the doppler method which is very effective for eliminating waves reflected from structural tissues.

Figure 6:
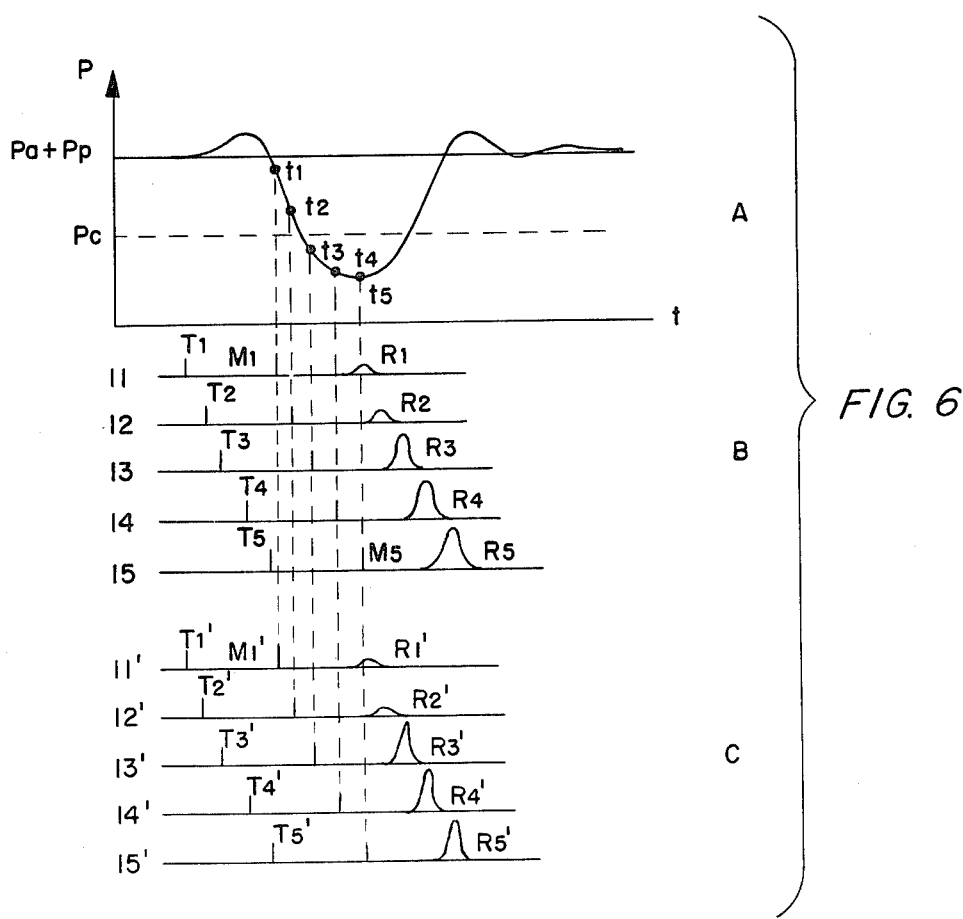
FIG. 6A illustrates the pressure waves form at the measuring region, when the pressure is swept by a pulse wave.
FIG. 6B is a diagram illustrating the timing of the bubble detecting signal.
FIG. 6C is a diagram illustrating the timing relation for detection with a Doppler signal.

If the applied pressure has a center frequency of 10 kHz and is swept to the negative direction sinusoidaly, the negative half cycle is about 50 μs. Therefore, a single detection can be obtained in a single sweep. The critical pressure can be detected by several sweeps and detections where the phases of the sending and receiving waves of the ultrasonic waves for both pressure sweep and detection are shifted a small amount each time. Details of these procedures are shown in FIG. 6. The heart pulsation is 1 to 2 times per second and therefore, it has a sufficient frequency for following dynamic changes of pressure. In order to detect, in detail, the status wherein the heart pressure rapidly changes, measurement can be made by shifting the phase so that the measuring points are sequentially placed in a rapidly changing period by synchronization with an electrocardiograph signal.

FIG. 6A shows how the sweep of the pressure is formed at the measuring area 4. The vertical axis indicates the absolute pressure (t), which is given as a sum of the atmospheric pressure $P_a$, the heart pressure $P_p(t)$ with reference to the atmospheric pressure and applied sweep pressure $-Q_0.\sin(2\pi ft)$. In this figure, $P_c$ is the bubbleforming critical pressure. The horizontal axis indicates the time t. When (t) is lower than the $P_c$, the bubbles are generated.

FIG. 6B shows the reflected signal extracted by the timing gate. The vertical axis indicates the amplitude, while the horizontal axis, the time. T is the time when the ultrasonic wave pulse is transmitted. M is the time when the send pulse reaches the measuring area 4. R is the time when the reflecting signal is received. If the distance between the transducer 5 and the measuring area 4 is l, the sound velocity is V, thus the time interval between T and R is given by 2 l/V and the following relation is obtained. T−M=M−R. Along axis 11 of FIG. 6B, the sending time $T_1$ is synchronized to the applied pressure waveform so that the measuring time $M_1$ coincides with the time T1 of the sweep pressure. The waveforms 12, 13 . . . are slso obtained in sequence, similarly shifting the time of $T_2, T_3, \ldots$ as shown in the figure. In the case of the waveforms 11 and 12 where (t) does not exceed $P_c$, the reflected signals $R_1$, $R_2$ are low in amplitude, but when (t) exceeds $P_c$, the waveforms 13, 14, and 15 give the intense reflected signals $R_3$, $R_4$ and $R_5$ because generated bubbles have very different accoustic impedances. FIG. 6C shows the waveforms obtained by extracting only the Doppler shift signals from the reflection signals of FIG. 6B. The signals $R_1'$, $R_2'$ are sufficiently small as compared with the $R_3'$, $R_4'$, $R_5'$, and improve the bubble detection accuracy.

In any case, when a pressure ($-Q_0.\sin 2\pi ft$) at each point ($t_1, t_2, \ldots$) of the pressure sweep waveform is previously known, $P_c$ can be obtained from the point where bubble generation starts.

In other way, $P_c$ can also be obtained from the minimum $Q_0$ for detecting bubble generation which can be obtained by adjusting such $Q_0$. In FIGS. 6B and C, the detecting waveforms 11, 12, . . . are overlapping in time in order to make clear the phase relation with the pressure sweep waveforms. In practice, the waveforms 11, 12, . . . are sent and received for different sweep cycles.

As another method, the condition of measuring point 4 can be measured continuously by sending the bubble detection ultrasonic wave as the continuous wave in place of the pulse as shown in FIG. 6. This embodiment is explained below, upon reference to FIG. 7.

In FIG. 7, 2 is a human body, 3 is the heart and 4 is the measuring area, selected in the blood flow in the left atrium in the figure. Numeral 1 is the ultrasonic transducer for pressure sweep and it is driven at a center frequency of 10 to 1000 kHz. The waveform is generated in the waveform generator 22. The waveform generator 22 digitally stores the waveforms which are converted from A to D in series and generates waveforms with a D/A conversion by sequentially reading the stored data. The center frequency can be changed by changing the period of the read clock. The amplifier 21 drives the transducer 1 through the power amplification of the waveform obtained from the waveform generator 22 and forms the necessary sweep negative pressure. Numeral 5 is the bubble detection probe. In this embodiment, the transmitting unit 5' and receiving unit 5" are provided individually and the continuous wave with M sequence modulation is transmitted and received. The base frequency generator 24 utilizes a crystal oscillation unit and it operates, for example, at 2 MHz. The M sequence modulation circuit, 25 sequentially reads the M sequence codes previously stored in the ROM in accordance with the clock from the timing control circuit 23 and, for example, phase-modulates the base sine signal. The power amplifier 26 drives the transmitter 5'. The receiving unit 5" receives signals which are amplified by the receiving amplifier circuit 27. The M sequence codes from the sequence modulation circuit 25 are sent to the multiplication circuit 30 via the variable delay circuit 28 which provides a delay equal to the traveling time of the sound forward and backward from transmitter to measuring area and back, by reffering the preset value specified with the ten-key in the depth setting circuit 29 and is compared with the output of the amplifier 27 by making a correlation between them. This is realized by the multiplication circuit 30. An output of the multiplication circuit 30 is orthogonally detected by 31 through comparison with the original oscillation signal. The real and imaginary part are sent to the amplitude circuit 32, where the square value of the amplitude is obtained by the integral circuit having a time constant shorter than the M sequence code length but longer than the code interval, for example, several tenths of a code length. The square-sum circuit, and the squared amplitude are used as the $Y_1$ signal.

The real or imaginary parts of the output of 31 are sent to the Doppler extraction circuit 33. This signal is detected after the band pass filter 31 which functions to limit higher frequencies, allowing the Doppler shift frequency to pass but not allowing the original oscillation frequency to pass. The bandpass filter 31 also functions to limit lower frequencies by not allowing the lower Doppler shift frequency to pass due to their stationary or almost stationary speed. This signal is then sent to $Y_2$ as the Doppler signal. If it is necessary to judge the direction of blood flow, both real and imaginary part are used.

The timing control circuit 23 generates the required clock signals from the original oscillation frequency of the base frequency generator 24, and also generates the control signals using the built-in program for each portion.

On the other hand, the actual pressure waveforms at each position of the measuring area 4 within the water caused by the transducer 1 are previously measured. These are stored, after the A/D conversion, into the sweep waveform storing circuit 34. The digitized waveforms are selected from the waveform storage circuit 34 corresponding to the depth preset by the depth setting circuit 29. These are read by the clocks which control the read start timing and the read speed provided by the timing control circuit 23, and the data obtained is D/A converted by the D/A converter 35 and is used as the X axis deflection signal (negative sweep pressure) for the CRT of the display unit 36. Numeral 36 is the two-channel synchroscope, giving respective outputs of the amplitude circuit 32 and the Doppler extraction circuit 33 to the $Y_1$ and $Y_2$ axis. From the $Y_1$-X and $Y_2$-X curves, the critical pressure $P_c$ can be confirmed, and the pressure $P_p$ can be obtained by reading the X values of the rising and falling points of the displayed curve. In this example, a manual judgment is made from the curve but is can be made automatically by the electronic means. Of course, $P_p$ can be digitally or analogously displayed and recorded continuously.

The B mode sector scan probe 50 is independent from said transducers 1 or 5. This is mechanically combined with 5 by the links and joints 51, 52 and 53 which joints have potentiometers giving the angular data. The position calculating circuit 54 calculates the relative position of transducers 5 and scan probe 50, and the data calculated is sent to the B mode display unit 55. The beam location of the transducer 5 is displayed as a line on the B mode display unit 56 and the position corresponding to the measuring area 4 is marked by increased brightness or by a marker in accordance with the depth information given by the depth setting circuit 29. This information is used for assigning the measuring area required on the sector scanned sectional view of a human body.

Moreover, the method of the present invention can also be used as a unique inspection or diagnostic means, very useful for tissue characterization and early detection of disease by executing measurements at each point in a bidimensional plane and by displaying the result on the display unit as a plane image.

In this case, it is easier and more effective to get the relative distribution of the critical pressure $P_c$ of bubble generation than it is to measure the absolute pressure of each point. Namely, in each organ of a living body, the composition and temperature of the cell liquid is different and the critical pressure $P_c$ is also different in each organ. But, it is not easy to obtain the critical pressure $P_c$ by calibrating it by using a separate measuring method at another measuring area as shown in the case of blood. In such a case, contrary to the measurement of blood pressure, the critical pressure $P_c$ can be measured relative to the atmospheric pressure, on the supposition that the absolute pressure is almost constant with respect to the atmospheric pressure (this condition is almost always true except for the area near the heart), and the tissue characterization can be made by observing the distribution in the bidimensional plane.

The critical pressure $P_c$ of each tissue changes as time ellapses, depending on total body activity, such as exercise, eating and sleeping etc. and this variation also appears in the blood. A clearer tissue characterization image, eliminating said aging variation, can be obtained by simultaneously measuring the critical pressure of the blood and displaying the critical pressure of each tissue with the relative value obtained from said critical value of blood.

Figure 8:
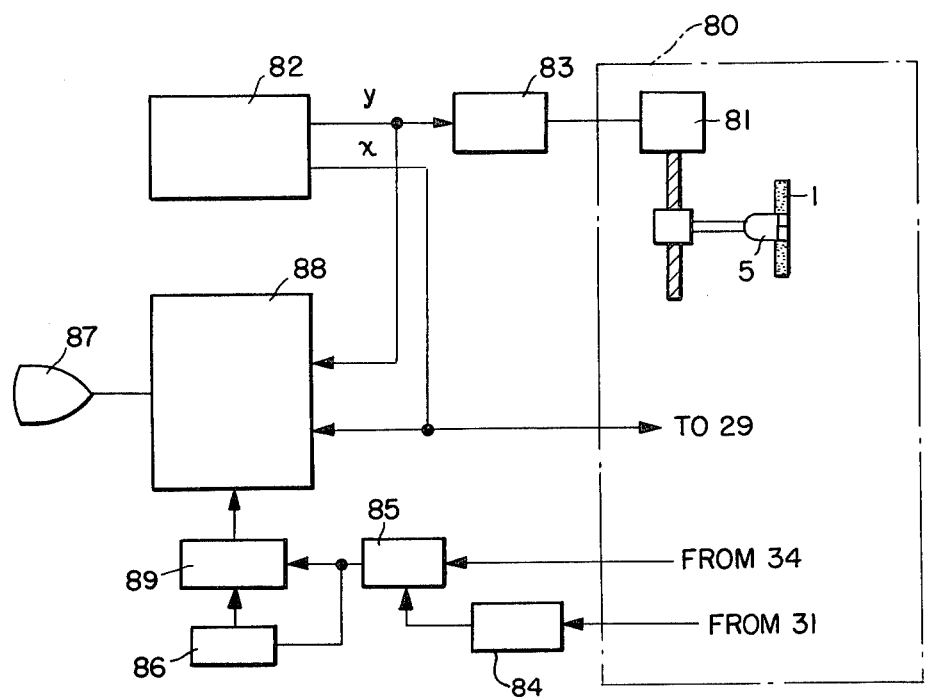
FIG. 8 is a block diagram of an embodiment for indicating pressure or tissue parameters relating the cavitation distribution two dimensionally.

FIG. 8 shows the block diagram of an embodiment for such object. The measuring system 80 is similar to that in FIG. 7. The only difference from FIG. 7 is that the low frequency and high frequency ultrasonic wave transducers 1 and 5 can move in the vertical direction by means of the pulse motor 81. In addition, the measuring location scanning control circuit 82 operates in such a manner as to sequentially advance y of the bidimensional coordinate (x, y) and also advance x at a high speed for each y.

The drive circuit 83 operates the pulse motor 81 and generates the specified number of pulses for each advance of y, shifting the transducers 1, 5 to the specified pitch. The bubble generating detection circuit 84 monitors the reflection of the high frequency ultrasonic waves sent from the orthogonal detection circuit 31 in FIG. 7 and detects the rise time. The sampling circuit 85 samples the low frequency ultrasonic wave amplitude sent from the sweep waveform storing circuit 34 in FIG. 7, namely the relative sweep pressure value as compared with the atmospheric pressure at the time when bubble generation is detected by said bubble detection circuit 84. Numeral 86 represents the measured-value temporary holding circuit, and numeral 89 represents the subtraction circuit. The bidimensional memory 88 to receives an output value of the subtraction circuit 89 which is then written at the address x, y. The display unit, 87 displays the measured value at each coordinate (x, y) stored in the bidimensional memory 88 in the brightness or color tone in accordance with the values as the plane image. A value of x from 82 is used to set the measuring area depth for 29 in FIG. 7.

In this embodiment, the transducers 1 and 5 are first applied to the upper part of arm in order to measure the critical pressure $P_c$ of the artery blood with the procedures explained for FIG. 7 and the value obtained is temporarily stored in the holding (register) circuit 86 as a reference. Thereafter, the transducers 1 and 5 are moved to the desired part of the body and the critical pressures of respective measuring areas are measured by sequentially changing x and y. These measured values are compared with the value in the register 86 by means of the subtraction circuit 89 and the difference obtained is written into the bidimensional memory. Instead of subtraction, the ratio of tissue critical pressure to blood critical pressue can be used.

According to the system as explained above, measurement for one display format can be realized in about 25 seconds, for example, by changing x, y respectively from 1 to 500 in order to obtain the picture elements of $500 \times 500$ and the continuous wave of 10 kHz is used as the low frequency ultrasonic wave. In practice, the propagation time is different for areas far from or near to the transducer, and some delay is caused by the drive of the pulse motor. Consequently, a little more time is required. A higher speed operation can also be realized by employing the phased array type transducers 1, 5. The scanning in the direction y is carried out electronically and measurements on individual points on the same line are carried out simultaneously by providing a plurality of pairs (for example, 500 pairs) of 27, 28, 29, 30, 31, 34, 84, 85 in FIG. 7. In this case, scanning is carried out for the polar coordinates in stead of the orthogonal coordinates and y is the deflection angle, while x is the distance from the center.

Since the critical pressure $P_c$ of tissue is generally comparatively low, it is practical to raise the critical pressure $P_c$ by dissolving an inert gas such as helium, krypton and xenon or carbon dioxide gas.

Moreover, the application field, which is similar to that of the tracer method using a radioactive isotope, can be developed by injecting a chemical substance which selectively works on the particular tissue and largely changes its critical pressure.

As explained above, according to the present invention, an inner pressure of an industrial system or a living body can be measured non-invasively by detecting an ultrasonic cavitation generated by an ultrasonic wave, resulting in the effect of measuring internal pressure safely without risk and without invading a system or causing a living body to come to death, moreover without causing a pain and without any fear of introducing impurities or infectious disease. In addition, since the measuring area can be changed from the outside, pressure distribution can also be measured on a real time basis.

It is also known that a high or low harmonic frequency ultrasonic wave is generated during bubble generation and/or collapsing. The high frequency ultrasonic wave unit 5' is no longer necessary, if such harmonic ultrasonic waves are used for the detection of bubbles.

I claim:
1. An ultrasonic pressure measuring system for measuring a pressure of a measuring area in a measuring medium, comprising:
   means for generating low frequency ultrasonic waves in the measuring medium, said low frequency ultrasonic waves generating fine bubbles which create high and low harmonic ultrasonic waves, in the measuring medium, the measuring medium having a critical pressure of bubble formation,
   means for generating high frequency ultrasonic waves in the measuring medium;
   means, operatively connected to the means for generating the low frequency ultrasonic waves and the means for generating the high frequency ultrasonic waves, for detecting the generation of the fine bubbles, and
   means, operatively connected to the means for detecting the generation of the fine bubbles, for measuring the pressure in the measuring area of the measuring medium in accordance with a relationship between the measuring medium pressure, the low frequency ultrasonic wave pressure, and the critical pressure of bubble formation.

2. A pressure measuring system according to claim 1, wherein
the fine bubbles are generated in the measuring medium by applying the low frequency ultrasonic waves to the medium in an area different from said measuring area, and
a pressure of the measuring medium in said different measuring area is measured by a separate method thereby establishing the relationship between the low frequency ultransonic wave pressure, the measuring medium pressure and the critical pressure of bubble formation.

3. A pressure measuring system according to claim 2 or 1, wherein the generation of bubbles is detected by applying high frequency ultrasonic waves and measuring a Doppler frequency shift included in a reflected wave of the high frequency ultrasonic waves.

4. A pressure measuring system according to claim 2, wherein
the time at which the fine bubbles are created in the measuring medium is determined by said detecting means operated at a plurality of different times during the period of said low frequency ultrasonic wave, and the relationship between the critical pressure of bubble formation and the measuring medium pressure is obtained from one of said plurality of different times.

5. A pressure measuring system according to claim 2, or 4, wherein the low frequency ultrasonic waves are pulse waves, having a center frequency under 1000 kHz and the high frequency ultrasonic waves have a center frequency of at least 100 kHz.

6. A pressure measuring system according to claim 2 or 4, wherein the measuring medium is the blood of a human body.

7. A pressure measuring system according to claim 2, wherein a substance which is easily soluble and easily generates bubbles is dissolved into said measuring medium prior to the pressure measurement.

8. A pressure measuring system according to claim 2, further comprising:
means for sequentially moving and setting the measuring area along a two-dimensional plane,
storage means, operatively connected to the means for sequentially moving and setting the measuring area and the measuring means, for sequentially storing a measured value at a measuring area corresponding to the coordinates of a position in said two-dimensional plane, and
means, operatively connected to the storing means, for displaying the measured values in accordance with such values as the coordinates of the two-dimensional plane.

9. A pressure measuring system according to claim 8, wherein
said measuring means further comprises a calculating means for measuring a first critical pressure of bubble formation of blood in a blood vessel of a living body the first critical pressure of bubble formation being stored in said storage means, and then measuring other critical pressures of bubble formation along the two-dimensional plane for the tissues at desired areas in said living body, and calculating the difference or ratio between each of the other critical pressures of bubble formation and the first critical pressure of bubble formation in the said storage means, storing the difference or ratio values in said storage means and then displaying the difference or ratio values by said display means.

10. A pressure measuring system according to claim 5, wherein the measuring medium is the blood of a human body.

11. A pressure measuring system according to claim 5, wherein a substance which is easily soluble and easily generates bubbles is dissolved into said measuring medium prior to a pressure measurement.

12. A pressure measuring system according to claim 6, wherein a substance which is easily soluble and easily generates bubbles is dissolved into said measuring medium prior to a pressure measurement.

13. A pressure measuring system according claim 2 or 4, wherein the low frequency ultrasonic waves are burst waves having a center frequency under 1000 KHz and the high frequency waves have a center frequency of at least 100 KHz.

14. A pressure measuring system according to claim 2 or 4, wherein the low frequency ultrasonic waves are continuous waves having a center frequency under 1000 KHz and the high frequency ultrasonic waves have a center frequency of at least 100 KHz.

15. A pressure measuring system according to claim 13, wherein the measuring medium is the blood of a human body.

16. A pressure measuring system according to claim 13, wherein a substance which is easily soluble and easily generates bubbles is dissolved into said measuring medium prior to a pressure measurement.

17. A pressure measuring system according to claim 14, wherein the measuring medium is the blood of a human body.

18. A pressure measuring system according to claim 14, wherein a substance which is easily soluble and easily generates bubbles is dissolved into said measuring medium prior to the pressure measurement.

19. An ultrasonic pressure measuring system for measuring a pressure of a measuring area in a measuring medium, comprising:
means for generating low frequency ultrasonic waves in the measuring medium, said low frequency ultrasonic waves generating fine bubbles, said fine bubbles creating high and low harmonic ultrasonic waves in the measuring medium, the measuring medium having a critical pressure of bubble formation,
means, operatively connected to the means for generating the low frequency ultrasonic waves, for detecting the generation of the fine bubbles, and
means, operatively connected to the means for detecting the generation of the fine bubbles, for measuring the pressure in the measuring area of the measuring medium in accordance with a relationship between the measuring medium pressure, the low frequency ultrasonic wave pressure, and the critical pressure of bubble formation.

20. A pressure measuring system according to claim 19, wherein
the fine bubbles are generated in the measuring medium by applying the low frequency ultrasonic waves to the medium in an area different from said measuring area, and
a pressure of the measuring medium in said different measuring area is measured by a separate method thereby establishing the relationship between the low frequency ultrasonic wave pressure, the measuring medium pressure and the critical pressure of bubble formation.

21. A pressure measuring system according to claim 20, wherein
the time at which the fine bubbles are created in the measuring medium is determined by said detecting means operated at a plurality of different times during the period of said low frequency ultrasonic wave and the relationship between the critical pressure of bubble formation and the measuring medium pressure is obtained from one of said plurality of different times.

22. A pressure measuring system according to claim 19, or 20, wherein the generation of bubbles is detected by the transmission of the high harmonic frequency ultrasonic waves generated by the bubbles.

23. A pressure measuring system according to claim 19 or 20, wherein the generation of bubbles is detected by the transmission of the low harmonic frequency ultrasonic waves generated by the bubbles.

24. A pressure measuring system according to claim 19 or 20, wherein the generation of bubbles is detected by the scattering of the high harmonic frequency ultrasonic waves generated by the bubbles.

25. A pressure measuring system according to claim 19 or 20, wherein the generation of bubbles is detected by the scattering of the low harmonic frequency ultrasonic waves generated by the bubbles.

26. A pressure measuring system according to claim 19 or 20, wherein the generation of bubbles is detected by the reflection of the high harmonic frequency ultrasonic waves generated by the bubbles.

27. A pressure measuring system according to claim 19 or 20, wherein the generation of bubbles is detected by the reflection of the low harmonic frequency ultrasonic waves generated by the bubbles.

28. A pressure measuring system according to claim 20 or 21, wherein the low frequency ultrasonic waves are pulse waves having a center frequency under 1000 kH$_z$.

29. A pressure measuring system according to claim 20 or 21, wherein the low frequency ultrasonic waves are burst waves having a center frequency under 1000 kH$_z$.

30. A pressure measuring system according to claim 20 or 21, wherein the low frequency ultrasonic waves are continuous waves having a center frequency under 1000 kH$_z$.

31. A pressure measuring system according to claim 20 or 21, wherein the measuring medium is the blood of a human body.

32. A pressure measuring system according to claim 28, wherein the measuring medium is the blood of a human body.

33. A pressure measuring system according to claim 29, wherein the measuring medium is the blood of a human body.

34. A pressure measuring system according to claim 30, wherein the measuring medium is the blood of a human body.

35. A pressure measuring system according to claim 20 or 21, wherein a substance which is easily soluble and easily generates bubbles is dissolved into said measuring medium prior to the pressure measurement.

36. A pressure measuring system according to claim 28, wherein a substance which is easily soluble and easily generates bubbles is dissolved into said measuring medium prior to the pressure measurement.

37. A pressure measuring system according to claim 29, wherein a substance which is easily soluble and easily generates bubbles is dissolved into said measuring medium prior to the pressure measurement.

38. A pressure measuring system according to claim 30, wherein a substance which is easily soluble and easily generates bubbles is dissolved into said measuring medium prior to the pressure measurement.

* * * * *

UNITED STATES PATENT AND TRADEMARK OFFICE
CERTIFICATE OF CORRECTION

PATENT NO. : 4,483,345

DATED : November 20, 1984

INVENTOR(S) : Miwa

It is certified that error appears in the above-identified patent and that said Letters Patent is hereby corrected as shown below:

Col. 4, line 22, (equation 2) "$(0 \leq \pi \, ft \leq \pi)$" should be --$(0 \leq 2\pi ft \leq \pi)$--.

Col. 5, line 50, after "and" (1st occurrence) insert --the--.

Col. 6, line 21, after "body" insert --,--;

line 54, ". is placed on the other side of the body" should be --the bag of water--.

Col. 8, line 25, "doppler" should be --Doppler--.

Col. 9, line 64, after "by" insert --band pass filter--.

Signed and Sealed this

Tenth Day of September 1985

[SEAL]

Attest:

DONALD J. QUIGG

Attesting Officer   Acting Commissioner of Patents and Trademarks - Designate